US00PP19808P2

(12) United States Plant Patent
Elsley

(10) Patent No.: US PP19,808 P2
(45) Date of Patent: Mar. 10, 2009

(54) ***EUPHORBIA* PLANT NAMED 'SHORTY'**

(50) Latin Name: *Euphorbia characias wulfenii*
Varietal Denomination: Shorty

(75) Inventor: John Elsley, Greenwood, SC (US)

(73) Assignee: ItSaul Plants LLC, Atlanta, GA (US)

( * ) Notice: Subject to any disclaimer, the term of this patent is extended or adjusted under 35 U.S.C. 154(b) by 0 days.

(21) Appl. No.: 12/080,154

(22) Filed: Mar. 31, 2008

(51) Int. Cl.
*A01H 5/00* (2006.01)

(52) U.S. Cl. ..... Plt./302

(58) Field of Classification Search ..... Plt./302
See application file for complete search history.

*Primary Examiner*—Annette H Para
(74) *Attorney, Agent, or Firm*—C. A. Whealy

(57) ABSTRACT

A new and distinct cultivar of *Euphorbia* plant named 'Shorty', characterized by its compact, upright to somewhat outwardly spreading plant habit; strong and sturdy flowering stems; short internodes; densely foliated; strong and healthy foliage; freely and uniformly flowering habit; green-colored inflorescences; and good garden performance.

1 Drawing Sheet

Botanical designation: *Euphorbia characias wulfenii.*
Cultivar denomination: 'SHORTY'.

BACKGROUND OF THE INVENTION

The present invention relates to a new and distinct cultivar of *Euphorbia*, botanically known as *Euphorbia characias wulfenii* and hereinafter referred to by the name 'Shorty'.

The new *Euphorbia* is a product of a planned breeding program conducted by the Inventor in Greenwood, S.C. The objective of the breeding program was to create new compact *Euphorbia* cultivars with relatively short flowering stems.

The new *Euphorbia* originated from a cross-pollination made by the Inventor in March, 2003 in Greenwood, S.C., of two unnamed *Euphorbia characias wulfenii* seedling selections, not patented. The new *Euphorbia* was discovered and selected by the Inventor as a single flowering plant within the progeny of the stated cross-pollination in a controlled environment in Greenwood, S.C. in February, 2004.

Asexual reproduction of the new *Euphorbia* by vegetative cuttings in a controlled environment in Dahlonega, Ga. since June, 2004, has shown that the unique features of this new *Euphorbia* are stable and reproduced true to type in successive generations.

SUMMARY OF THE INVENTION

The cultivar Shorty has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Shorty'. These characteristics in combination distinguish 'Shorty' as a new and distinct cultivar of *Euphorbia:*

1. Compact, upright to somewhat outwardly spreading plant habit.
2. Strong and sturdy flowering stems.

3. Short internodes, densely foliated.
4. Strong and healthy foliage.
5. Freely and uniformly flowering habit.
6. Green-colored inflorescences.
7. Good garden performance.

Plants of the new *Euphorbia* differ primarily from plants of the parent selections in plant height and flowering habit as plants of the new *Euphorbia* are more compact and have shorter flowering stems than plants of the parent selections. In addition, plants of the new *Euphorbia* are stronger and sturdier than plants of the parent selections.

Plants of the new *Euphorbia* can be compared to plants of the *Euphorbia characias wulfenii* cultivar Tasmanian Tiger, disclosed in U.S. Plant Pat. No. 5,715. Plants of the new *Euphorbia* and the cultivar Tasmanian Tiger differ in the following characteristics:

1. Plants of the new *Euphorbia* and the cultivar Tasmanian Tiger differ in foliage color as plants of the cultivar Tasmanian Tiger have white and grey-green variegated foliage.
2. Plants of the new *Euphorbia* and the cultivar Tasmanian Tiger differ in flower color as plants of the cultivar Tasmanian Tiger have cream-colored flowers.

BRIEF DESCRIPTION OF THE PHOTOGRAPH

The accompanying colored photograph illustrates the overall appearance of the new *Euphorbia*, showing the colors as true as it is reasonably possible to obtain in colored reproductions of this type. Colors in the photograph may differ slightly from the color values cited in the detailed botanical description which accurately describe the colors of the new *Euphorbia*. The photograph comprises a side perspective view of a typical flowering plant of 'Shorty' grown in a container.

DETAILED BOTANICAL DESCRIPTION

The aforementioned photograph and following observations, measurements and values describe plants grown in containers in Tolar, Tex., under conditions which approximate commercial practice during the autumn and winter in an outdoor nursery. Plants had been growing for about two years when the photograph and description were taken. In the following description, color references are made to The Royal Horticultural Society Colour Chart, 2001 Edition, except where general terms of ordinary dictionary significance are used.

BOTANICAL CLASSIFICATION *Euphorbia characias wulfenii* cultivar Shorty.

PARENTAGE:

*Female, or seed, parent.*—Unnamed *Euphorbia characias wulfenii* seedling selection, not patented.

*Male, or pollen, parent.*—Unnamed *Euphorbia characias wulfenii* seedling selection, not patented.

Propagation:

*Type.*—By vegetative cuttings.

*Time to produce a rooted young plant, summer.*—About four months at 18° C. to 24° C.

*Time to produce a rooted young plant, winter.*—About five to six months at 7° C. to 10° C.

*Root description.*—Fibrous; new roots, white, becoming cinnamon brown with development.

*Rooting habit.*—Not freely branching; sparse to moderately dense.

Plant description:

*Plant form and growth habit.*—Compact and mounded plant habit; upright to somewhat outwardly spreading; broadly inverted triangle; herbaceous, woody-based perennial subshrub. Relatively short, strong and sturdy flowering stems. Moderately vigorous growth rate.

*Branching habit.*—Freely basal branching, usually about 30 basal branches develop per plant; dense and bushy plant form.

*Plant height.*—About 36 cm.

*Plant diameter.*—About 45 cm.

*Basal branch description.*—Length: About 34 cm. Diameter: About 7 mm. Internode length: About 3 mm. Strength: Strong. Texture: Smooth, glabrous. Color, developing stems: Close to 145A. Color, older stems: Close to 187C.

*Foliage description.*—Arrangement: Whorled in close spirals; simple; densely foliated. Length: About 4.3 cm. Width: About 5 mm. Shape: Lanceolate. Apex: Acute. Base: Attenuate. Margin: Entire. Texture, upper and lower surfaces: Pubescent; velvety. Venation: Pinnate. Color: Developing and fully expanded foliage, upper surface: Close to 147A; venation, close to 145A. Developing and fully expanded foliage, lower surface: Close to 147B; venation, close to 146D. Petiole: Length: About 4 mm. Diameter: About 2 mm. Texture, upper and lower surfaces: Pubescent. Color, upper surface: Close to 144C. Color, lower surface: Close to 154D.

Inflorescence description:

*Natural flowering season.*—In northern Texas, flowering occurs during the early and mid-spring; flowering uniform with most inflorescences in flower at the same time.

*Arrangement.*—Cyathium with subtending green-colored flower bracts arranged in umbellate terminal clusters and also singly arising from leaf axils immediately below the terminal clusters. Cyathium with female flowers. Freely flowering with about 40 cyathium per basal branch. Each cyathium developing two more "new" pistillate flowers after pistil senescence; said "new" pistillate flowers each developing two more pistillate flowers after their pistil senescence; process continuously repeating throughout flowering period. Inflorescences face mostly upright. Inflorescences persistent. Inflorescences fragrant, slightly unpleasant.

*Terminal cluster height.*—About 7.7 cm.

*Terminal cluster diameter.*—About 7.2 cm.

*Cyathium diameter* (*including flower bracts*).—About 1.6 cm.

*Cyathium depth* (*including reproductive organs*).—About 2 cm.

*Flower longevity on the plant.*—About four weeks.

*Flower bracts.*—Quantity/arrangement: Two; opposite. Length: About 8 mm. Width: About 1.2 cm. Shape: Semi-circular. Apex: Rounded with slight central notch. Base: Fused. Margin: Entire. Texture, upper and lower surfaces: Glabrous; smooth. Color: When opening and fully expanded, upper surface: More green than 141A. When opening and fully opened, lower surface: More green than 138A.

*Peduncles.*—Length: About 3.6 cm. Diameter: About 1 mm. Strength: Strong. Angle: Erect to about 45° from vertical. Texture: Smooth, glabrous. Color: Close to 143A.

*Reproductive organs.*—Androecium: None observed. Gynoecium: Quantity: One per cyathia. Pistil length: About 6 mm. Style length: About 2.5 mm. Style color: Close to 144B. Stigma shape: Six-parted. Stigma color: Close to 144B to 144C. Ovary color: Close to 144C.

*Seed/fruit.*—Seed and fruit development have not been observed.

Disease/pest resistance: Plants of the new *Euphorbia* have not been observed to be resistant to pathogens and pests common to *Euphorbia*.

Garden performance: Plants of the new *Euphorbia* have been observed to have good garden performance and tolerate rain, wind and high temperatures of about 40° C. Plants of the new *Euphorbia* have been observed to be hardy to USDA Zone 8.

It is claimed:

1. A new and distinct *Euphorbia* plant named 'Shorty' as illustrated and described.

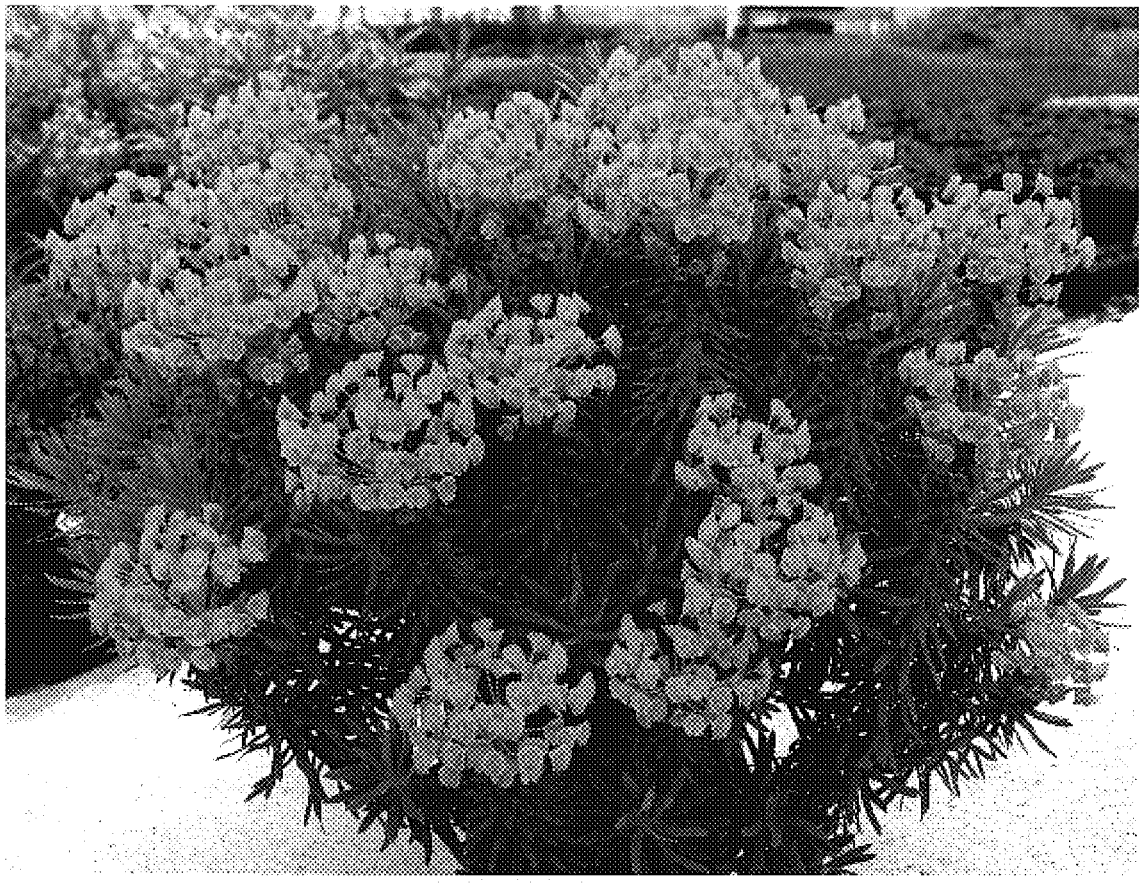

* * * * *